US008383891B2

(12) United States Patent
Cahoon et al.

(10) Patent No.: US 8,383,891 B2
(45) Date of Patent: Feb. 26, 2013

(54) WUSCHEL (WUS) GENE HOMOLOGS

(75) Inventors: Rebecca E. Cahoon, Lincoln, NE (US);
William James Gordon-Kamm, Urbandale, IA (US); Keith S. Lowe, Johnston, IA (US); Christopher Jay Scelonge, Des Moines, IA (US); Yumin Tao, Ames, IA (US)

(73) Assignees: E.I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 13/168,133

(22) Filed: Jun. 24, 2011

(65) Prior Publication Data

US 2011/0258741 A1    Oct. 20, 2011

Related U.S. Application Data

(63) Continuation of application No. 12/018,292, filed on Jan. 23, 2008, now Pat. No. 7,994,391, which is a continuation of application No. 09/807,946, filed as application No. PCT/US00/26648 on Sep. 28, 2000, now Pat. No. 7,348,468.

(60) Provisional application No. 60/157,216, filed on Oct. 1, 1999.

(51) Int. Cl.
*C12N 15/29* (2006.01)
*C12N 15/82* (2006.01)
*A01H 5/00* (2006.01)
*A01H 5/10* (2006.01)

(52) U.S. Cl. ........ 800/298; 800/278; 800/314; 800/287; 536/23.1; 536/23.6; 435/320.1

(58) Field of Classification Search ........................ None
See application file for complete search history.

(56) References Cited

U.S. PATENT DOCUMENTS 5,929,301 A    7/1999 Baszcynski et al.
2004/0166563 A1    8/2004 Lowe et al.

OTHER PUBLICATIONS

Bowie et al, Science 247:1306-1310, 1990.*
McConnell et al, Nature 411 (6838):709-713, 2001.*
Kamiya et al (2003, The Plant Journal 35:429-441).*
Gidoni et al (2001 Euphytica 121: 145-156).*
Endrizzi, K., "The Shoot Meristemless Gene is Required for Maintenance of Undifferentiated Cells in *Arabidopsis* Shoot and Floral Meristems and Acts at a Different Regulatory Level than the Meristem Genes Wuschel and Zwille"; The Plant Journal (1996) 10:967-979.
Brand, U., "Dependence of Stem Cell Fate in *Arabidopsis* on a Feedback Loop Regulated by CLV3 Activity"; Science (2000) 289:617-619.
Schoof, H., "The Stem Cell Population of *Arabidopsis* Shoot Meristems is Maintained by a Regulatory Loop Between the Clavata and Wuschel Genes"; Cell (2000) 100:635-644.
Lin, X., et al.; "Sequence and Analysis of Chromosome 2 of the Plant *Arabidopsis thaliana*"; National Center for Biotechnology Information General Identifier No. 3785979; Apr. 5, 2000.
Lin, X., et al., "Sequence and Analysis of Chromosome 2 of the Plant *Arabidopsis thaliana*"; Nature (1999) 402:761-768.
Laux, T., et al.; "Role of Wuschel in Regulating Stem Cell Fate in the *Arabidopsis* Shoot Meristem"; National Center for Biotechnology Information General Identifier No. 4090200; Dec. 30, 1998.
Lin, X., et al.; "Sequence and Analysis of Chromosome 2 of the Plant *Arabidopsis thaliana*"; National Center for Biotechnology Information General Identifier No. 4580396; Apr. 5, 2000.
Sata, S., et al.; "Structural Analysis of *Arabidopsis thaliana* Chromosome 3. I. Sequence Features the Regions of 4,504,864 BP Covered by Sixty P1 and TAC Clones"; National Center for Biotechnology Information General Identifier No. 9294502; Dec. 27, 2000.
Sato, S., et al.; "Structural Analysis of *Arabidopsis thaliana* Chromosome 3. I. Sequence Features of the Regions of 4,504,864 BP Covered by Sixty P1 and TAC Clones"; DNA Research (2000) 7:131-135.
Lin, X. et al.; "*Arabidopsis thaliana* Chromosome III BAC T12J13 Genomic Sequence"; National Center for Biotechnology Information General Identifier 6091768; Jan. 24, 2001.
Hsing, Y.C., et al.; "*Oryza sativa* PAC P0699E04 Genomics Sequence, Complete Sequence"; National Center for Biotechnology Information General Identifier No. 8099120; Aug. 7, 2000.
Bidney, D., et al.; "Microprojectile Bombardment of Plant Tissues Increases Transformation Frequency by *Agrobacterium tumefaciens*"; Plant Molecular Biology (1992) 18:301-313.
Burrus, M., et al.; "Regeneration of Fertile Plant From Protoplasts of Sunflower"; Plant Cell (1991) 10:161-166.
Sugiura, M., et al.; "Purification and Properties of Oxalate Oxidase from Barley Seedlings"; Chem. Pharm. Bull. (1979) 27:2003-2007.
Wohlleben, W., et al.; "Nucleotide Sequence of the Phosphinothricin N-Acetyltransferase Gene from *Streptomyces virido-chromogenes* Tu494 and its Expression in *Nicotiana tabacum*"; Gene (1988) 70:25-37.
Lowe, K., et al.; "Transformation of the Maize Apical Meristem: Transgenic Sector Reorganization and Germline Transmission"; Genetic Biotechnology and Breeding of Maize and Sorghum (1997) 94-97.
Mayer, K.F.X., et al.; "Role of Wuschel in Regulating Stem Cell Fate in the *Arabidopsis* Shoor Meristem" Cell (1998) 95:805-815.
Laux, T., et al.; "The Wuschel Gene is Required for Shoot and Floral Meristem Integrity in *Arabidopsis*" *Arabidopsis* Development (1996) 122:87-96.
De La Bastide, M., et al.; "*A. thaliana* BAC T13L16 from Chromosome IV, Top Arm"; EMBL Sequence Library Database Accession No. AC003952; Jan. 9, 1999.

(Continued)

*Primary Examiner* — Stuart F Baum

(57) ABSTRACT

This invention relates to isolated polynucleotides encoding WUS polypeptides. The invention further provides isolated WUS polypeptides. The invention also provides methods of using the polynucleotides to modulate the level of WUS, improve transformation efficiency, to stimulate plant cell growth, including stem cells, to stimulate organogenesis, to stimulate somatic embryogenesis, to induce apomixis, and to provide a positive selection for cells comprising the polynucleotide. The invention also relates to cells, plants and seeds comprising the polynucleotides of the invention or produced by the methods of the invention.

14 Claims, 2 Drawing Sheets

OTHER PUBLICATIONS

De La Bastide, M., et al.; "*A. thaliana* BAC T13L16 from Chromosome IV, Top Arm"; EMBL Sequence Library Database Accession No. T00829; Apr. 30, 1999.

Bowie, James U. et al., "Deciphering the Message in Protein Sequences: Tolerance to Amino Acid Substitutions"; Science, Mar. 16, 1990, pp. 1306-1310, vol. 247, No. 4948.

Kamiya, Noriko et al., "Isolation and characterization of a rice WUSCHEL-type homeobox gene that is specifically expressed in the central cells of a quiescent center in the root apical meristem", The Plant Journal, 2003, pp. 429-441, vol. 35.

McConnell, Jane R. et al., "Role of PHABULOSA and PHAVOLUTA in determining radial patterning in shoots", Nature, Jun. 2001, pp. 709-713, vol. 411(6838).

\* cited by examiner

FIG. 1A

```
                *    *****  *****************  **              *          *******  ***
SEQ ID NO:04    MEALS---------------------------------------------------------------------
SEQ ID NO:10    MEG-----------------------------------------------------------------------
SEQ ID NO:20    MESHS-----------------------------------------------GLSPERHAAAE-----------
SEQ ID NO:22    MKVHQFARGF-WEHEPSLTLGCKRLRPLAPKLSNTDTISPPHHPVTTFDLKSFIKPESAS
SEQ ID NO:24    MKVHQFTRGLIWEHEPFLTLGCKRLRPLAPKLPNTKTITTP-----FDLKSFIRPESGP
SEQ ID NO:25    MEPPQHQH-----------------------------------------HHH---------
                1                                                              60

**                          *           **  ** **              *
SEQ ID NO:04    ----G-------RVGVKC----------------GRWNPTAEQVKVLTELF-RAGLRTPSTEQ
SEQ ID NO:10    ---------------------------PVRSRWTPKPEQILILESIF-NSGMVNPPKDE
SEQ ID NO:20    ----SDAEAENVRTHSSV----------------SRWSPTKEQIDMLENLY-KQGIRTPSTEQ
SEQ ID NO:22    RKLGIGSSDDNTNKRDPSSPQGQAETHIPGGTRWNPTQEQIGILEMLY-RGGMRTPNAQQ
SEQ ID NO:24    RK------PVSSDDTKKDPPSPQGQIETH-PGGTRWNPTQEQIGILEMLY-KGGMRTPNAQQ
SEQ ID NO:25    --------QADQESGNNNNKSGSGGYTCR-QTSTRWTPTTEQIKILKELYYNNAIRSPTADQ
                61                                                            120

*        *       *********    * *
SEQ ID NO:04    IQRISTHLSAFGKVESKNVFYWFQNHKARERHHHK-KRRRGASSSSPDSGSGRGSNNEED
SEQ ID NO:10    TVRIRKLLERFGAVGDANVFYWFQNRRSRSRRQRQLQAQAAASSSSGSPPTSGLAPGH
SEQ ID NO:20    IQQITSRLRAYGHIEGKNVFYWFQNHKARQRQKLM-KQQTIAYSNR----FLRASHPICQ
SEQ ID NO:22    IEQITAQLSKYGKIEGKNVFYWFQNHKARERQKQ--KRNNLGLAHSPRTLTTSPPFSC-
SEQ ID NO:24    IEQITVQLGKYGKIEGKNVFYWFQNHKARERQKQ--KRSSLASSHSPRTPTIHS------
SEQ ID NO:25    IQKITARLRQFGKIEGKNVFYWFQNHKARERQKKRFNGTNMTTPSSSPNSVMMAANDHYH
                121                                                          180
```

FIG. 1B

```
SEQ ID NO:04   ---GRGAASQSHDAD-ADADLVLQPPESKREARS--YG--HHHRL--------------------
SEQ ID NO:10   ATASSTAGMFAHGATYGSSASASWPPPPSCEGMGDLDYGGGDDLFAISRQMGYASGGGS
SEQ ID NO:20   ---NVACAPYCLQ----RSGFSFYPQQSKVLASGGIS--STGPL--------------------
SEQ ID NO:22   ---CVITTMDTT--KRGEVV------ERE-EEDSPLK--K-CR---------------------
SEQ ID NO:24   ------VVTLETT--RGEVV------ERDHEEDSPYK--KKCR---------------------
SEQ ID NO:25   PLLHHHHGVPMQRPA-NSVNVKLNQDHHLYHHNKPYPSFNNGNLNHASSGTECGVVNASN
                                                                              240
                                                            *  *
               181

SEQ ID NO:04   --VTCYVRDVVEQQ-------EASPSWERPTRE--------VETLELFPLKSYGDLE--A
SEQ ID NO:10   GSASSAAVAHHEQQQLYYSP-----------CQPASMTVFINGVATEVPRGPIDLRSMF
SEQ ID NO:20   --G--MQRMFDGM--------QSS----EHPDCN---------REVLTLFPLHPTGILKEKT
SEQ ID NO:22   -----SWAFEYLEDQ---------R-----EE--E---------HRTLELFPLHPEG-------
SEQ ID NO:24   -----RWVFDCLEEQ--------NMSSPCEQE--E---------HRTLELFPLHPEG-------
SEQ ID NO:25   GYMSSHVYGSMEQDCSMNYNNVGGWANMDHHYSSAPYNFFDRAKPLFGLEGHQDEEECG
                      *                    *                              ****  *
                                                                              300
               241

SEQ ID NO:04   AEKVRSYVRGIA----ATS----EQCRELS---FFDVSAGRDPP---LELRLCSFGP
SEQ ID NO:10   GQDVMLVHSTAGLLPVNEYGVLTQSLQMGESYF-------------------LVTRGY
SEQ ID NO:20   THQVPSLASTSV----VAV----DEDGHLGNQPFFNFFTTEPRS---RE-------R-
SEQ ID NO:22   ----------------------------------------------------------R-
SEQ ID NO:24   ----------------------------------------------------------R-
SEQ ID NO:25   GDAYLEHRRTLPLFPMHG----EDHINGGSGAIWKYGQSEVRPCASLELRL----N
                                                                         356
               301
```

WUSCHEL (WUS) GENE HOMOLOGS

CROSS-REFERENCE TO RELATED APPLICATIONS

This application is a continuation of U.S. application Ser. No. 12/018,292, filed Jan. 23, 2008, now U.S. Pat. No. 7,994,391, which is a continuation of U.S. application Ser. No. 09/807,946, filed Apr. 20, 2001, now U.S. Pat. No 7,348,468, which is the National Stage of International Application Number PCT/US00/26648, filed Sep. 28, 2000, which claims the benefit under 35 U.S.C. §119(e) of U.S. Provisional Application No. 60/157,216, filed Oct. 1, 1999, the disclosures of which are all herein incorporated in their entirety by reference.

FIELD OF THE INVENTION

This invention is in the field of plant molecular biology. More specifically, this invention pertains to nucleic acid fragments encoding Wuschel (WUS) proteins in plants and seeds.

BACKGROUND

Organ formation in plants occurs via the activity of apical meristems. Plant meristems contain a pool of stem cells, which are able to self-maintain, give rise to a variety of cell types including cells required for organ initiation. The initiation and maintenance of stem cells and their integration into organ-forming meristems are thus the basis for continuous plant development.

The Wuschel protein, designated hereafter as WUS, plays a key role in the initiation and maintenance of the apical meristem, which contains a pool of pluripotent stem cells (Endrizzi, et al., (1996) *Plant Journal* 10:967-979; Laux, et al., (1996) *Development* 122:87-96; and Mayer, et al., (1998) *Cell* 95:805-815). *Arabidopsis* plants mutant for the WUS gene contain stem cells that are misspecified and that appear to undergo differentiation. WUS encodes a novel homeodomain protein which presumably functions as a transcriptional regulator (Mayer, et al., (1998) *Cell* 95:805-815). The stem cell population of *Arabidopsis* shoot meristems is believed to be maintained by a regulatory loop between the CLAVATA (CLV) genes which promote organ initiation and the WUS gene which is required for stem cell identity, with the CLV genes repressing WUS at the transcript level, and WUS expression being sufficient to induce meristem cell identity and the expression of the stem cell marker CLV3 (Brand, et al., (2000) *Science* 289:617-619; Schoof, et al., (2000) *Cell* 100:635-644). Constitutive expression of WUS in *Arabidopsis* has been recently shown to lead to adventitious shoot proliferation from leaves (in planta) (Laux, T., Talk Presented at the XVI International Botanical Congress Meeting, Aug. 1-7, 1999, St. Louis, Mo.).

There is a great deal of interest in identifying the genes that encode proteins involved in development in plants, generally toward the objective of altering plant growth and architecture. WUS represents one such gene. However, the WUS gene can also be used for the novel application of stimulating in vitro growth of plant tissue and improving transformation. In this manner, this gene can expand the range of tissues types targeted for transformation. Specifically, the WUS gene may be used to improve meristem transformation frequencies and could result in genotype independent transformation of many important crops such as maize, soybean and sunflower. Furthermore, transformation into meristems would stimulate the formation of new apical initials reducing the chimeric nature of the transgenic events. Lastly, ectopic expression into non-meristematic cells would stimulate adventive meristem formation. This could lead to transformation of non-traditional tissues such as leaves, leaf bases, stem tissue, etc. Alternatively, transformation of a more traditional target such as callus or the scutellum of immature embryos could promote a "non-traditional" growth response, i.e., meristems in place of somatic embryos. In addition, WUS may also be used as a genetic marker for meristems. Accordingly, the availability of nucleic acid sequences encoding all or a portion of a WUS protein would facilitate studies to better understand programmed development in plants, provide genetic tools to enhance the efficiency of gene transfer into meristem tissue and help provide alternative transformation methods in several important crops.

SUMMARY

The present invention concerns an isolated polynucleotide comprising a nucleotide sequence selected from the group consisting of: (a) a first nucleotide sequence encoding a polypeptide of at least 50 amino acids having at least 70% identity based on the Clustal method of alignment when compared to a polypeptide selected from the group consisting of SEQ ID NOS: 2, 4 and 12; (b) a second nucleotide sequence encoding a polypeptide of at least 100 amino acids having at least 70% identity based on the Clustal method of alignment when compared to a polypeptide selected from the group consisting of SEQ ID NOS: 14, 16, 18 and 20; (c) a third nucleotide sequence encoding a polypeptide of at least 180 amino acids having at least 70% identity based on the Clustal method of alignment when compared to a polypeptide of SEQ ID NO: 24; (d) a fourth nucleotide sequence encoding a polypeptide of at least 230 amino acids having at least 70% identity based on the Clustal method of alignment when compared to a polypeptide of SEQ ID NO: 22; (e) a fifth nucleotide sequence encoding a polypeptide of at least 100 amino acids having at least 80% identity based on the Clustal method of alignment when compared to a polypeptide selected from the group consisting of SEQ ID NOS: 6, 8 and 10; and (f) a sixth nucleotide sequence comprising the complement of (a), (b), (c), (d) or (e).

In a second embodiment, it is preferred that the isolated polynucleotide of the claimed invention comprises a first nucleotide sequence which comprises a nucleic acid sequence selected from the group consisting of SEQ ID NOS: 1, 3, 5, 7, 9, 11, 13, 15, 17, 19, 21 and 23 that codes for the polypeptide selected from the group consisting of SEQ ID NOS: 2, 4, 6, 8, 10, 12, 14, 16, 18, 20, 22 and 24.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOS: 1, 3, 5, 7, 9, 11, 13, 15, 17, 19, 21 and 23 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns an isolated WUS polypeptide selected from the group consisting of: (a) a polypeptide of at least 50 amino acids having at least 70% identity based on the Clustal method of alignment when compared to a polypeptide selected from the group consisting of SEQ ID NOS: 2, 4 and 12; (b) a polypeptide of at least 100 amino acids having at least 70% identity based on the Clustal method of alignment when compared to a polypeptide selected from the group consisting of SEQ ID NOS: 14, 16, 18 and 20; (c) a polypeptide of at least 180 amino acids having at least 70% identity based on the Clustal method of alignment when compared to a polypeptide of SEQ ID NO:24; (d) a polypeptide of at least 230 amino acids having at least 70% identity based on the Clustal method of alignment when compared to a polypeptide of SEQ ID NO: 22; and (e) a polypeptide of at least 100 amino acids having at least 80% identity based on the Clustal method of alignment when compared to a polypeptide selected from the group consisting of SEQ ID NOS: 6, 8 and 10.

In an eighth embodiment, the invention relates to a method of selecting an isolated polynucleotide that affects the level of expression of a WUS polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the WUS polypeptide or enzyme activity in the host cell containing the isolated polynucleotide; and (d) comparing the level of the WUS polypeptide or enzyme activity in the host cell containing the isolated polynucleotide with the level of the WUS polypeptide or enzyme activity in the host cell that does not contain the isolated polynucleotide.

In a ninth embodiment, the invention concerns a method of obtaining a nucleic acid fragment encoding a substantial portion of a WUS polypeptide, preferably a plant WUS polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOS: 1, 3, 5, 7, 9, 11, 13, 15, 17, 19, 21 and 23, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a WUS amino acid sequence.

In a tenth embodiment, this invention relates to a method of obtaining a nucleic acid fragment encoding all or a substantial portion of the amino acid sequence encoding a WUS polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the WUS polynucleotide in an amount sufficient to complement a null mutant to provide a positive selection means.

In a thirteenth embodiment, this invention relates to a method of altering the level of expression of a WUS protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the WUS protein in the transformed host cell.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A and 1B show an alignment of the amino acid sequences of WUS protein encoded by the nucleotide sequences derived from corn clone cpi1c.pk012.p19 (SEQ ID NO: 4), corn clone p0058.chpab57r (SEQ ID NO: 10), soybean clone ses4d.pk0033.c8 (SEQ ID NO: 20), soybean clone sgs5c.pk0002.f2 (SEQ ID NO: 22), and a contig assembled using soybean clone ssm.pk0060.h4 and NCBI GenBank Identifier (GI) No. 4395781 (SEQ ID NO: 24), and the WUS protein from *Arabidopsis thaliana* (NCBI GI No. 4090200; SEQ ID NO: 25). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs or PCR fragment sequence ("Contig*"), or sequences encoding the entire protein derived from an EST, an FIS, a contig, or an FIS and PCR fragment sequence ("CGS"). Nucleotide SEQ ID NOS: 1, 5, 11 and 15 correspond to nucleotide SEQ ID NOS: 1, 3, 5 and 7, respectively, presented in U.S. Provisional Application No. 60/157,216, filed Oct. 1, 1999. Amino acid SEQ ID NOS: 2, 6, 12 and 16 correspond to amino acid SEQ ID NOS: 2, 4, 6 and 8, respectively, presented in U.S. Provisional Application No. 60/157,216, filed Oct. 1, 1999. The sequence descriptions and Sequence Listing attached hereto comply with the rules governing nucleotide and/or amino acid sequence disclosures in patent applications as set forth in 37 C.F.R. §1.821-1.825.

TABLE 1

WUS Proteins

| Protein (Plant Source) | Clone Designation | Status | SEQ ID NO: (Nucleotide) | SEQ ID NO: (Amino Acid) |
|---|---|---|---|---|
| WUS Protein (Corn) | Contig of cpg1c.pk006.b16 cpi1c.pk012.p19 | Contig | 1 | 2 |
| WUS Protein (Corn) | cpi1c.pk012.p19 (FIS) | CGS | 3 | 4 |
| WUS Protein (Corn) | p0016.ctsas50r | EST | 5 | 6 |
| WUS Protein (Corn) | p0016.ctsas50r | FIS | 7 | 8 |
| WUS Protein (Corn) | p0058.chpab57r (FIS) | CGS | 9 | 10 |
| WUS Protein (Corn) | p0083.cldev71r | EST | 11 | 12 |
| WUS Protein (Corn) | p0083.cldev71r | FIS | 13 | 14 |
| WUS Protein (Soybean) | Contig of scr1c.pk001.d2 ses4d.pk0033.c8 | Contig | 15 | 16 |
| WUS Protein (Soybean) | scr1c.pk001.d2 | FIS | 17 | 18 |
| WUS Protein (Soybean) | ses4d.pk0033.c8 (FIS) | CGS | 19 | 20 |
| WUS Protein (Soybean) | sgs5c.pk0002.f2 (EST) | CGS | 21 | 22 |
| WUS Protein (Soybean) | Contig of ssm.pk0060.h4 (FIS) NCBI GI No. 4395781 | CGS | 23 | 24 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

DETAILED DESCRIPTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOS: 1, 3, 5, 7, 9, 11, 13, 15, 17, 19, 21 or 23, or the complement of such sequences.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOS: 1, 3, 5, 7, 9, 11, 13, 15, 17, 19, 21 and 23, and the complement of such nucleotide sequences may be used in methods of selecting an isolated polynucleotide that affects the expression of a WUS polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 or 180 amino acids, still more preferably at least 200 or 230 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul, et al., (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster, (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see, U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel, (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere, et al., (1987) *Meth. Enzymol.* 143:277) and particle-accelerated or "gene gun" transformation technology (Klein, et al., (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels, et al., Cloning Vectors: A Laboratory Manual, 1985, supp. 1987; Weissbach and Weissbach, Methods for Plant Molecular Biology, Academic Press, 1989; and Flevin, et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook, et al., *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 50 amino acids having at least 70% identity based on the Clustal method of alignment when compared to a polypeptide selected from the group consisting of SEQ ID NOS: 2, 4 and 12; (b) a second nucleotide sequence encoding a polypeptide of at least 100 amino acids having at least 70% identity based on the Clustal method of alignment when compared to a polypeptide selected from the group consisting of SEQ ID NOS: 14, 16, 18 and 20; (c) a third nucleotide sequence encoding a polypeptide of at least 180 amino acids having at least 70% identity based on the Clustal method of alignment when compared to a polypeptide of SEQ ID NO: 24; (d) a fourth nucleotide sequence encoding a polypeptide of at least 230 amino acids having at least 70% identity based on the Clustal method of alignment when compared to a polypeptide of SEQ ID NO: 22; (e) a fifth nucleotide sequence encoding a polypeptide of at least 100 amino acids having at least 80% identity based on the Clustal method of alignment when compared to a polypeptide selected from the group consisting of SEQ ID NOS: 6, 8 and 10; and (f) a sixth nucleotide sequence comprising the complement of (a), (b), (c), (d) or (e).

Preferably, the first nucleotide sequence comprises a nucleic acid sequence selected from the group consisting of SEQ ID NOS:1, 3, 5, 7, 9, 11, 13, 15, 17, 19, 21 and 23, that codes for the polypeptide selected from the group consisting of SEQ ID NOS: 2, 4, 6, 8, 10, 12, 14, 16, 18, 20, 22 and 24.

Nucleic acid fragments encoding at least a portion of several WUS proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other WUS proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman, et al., (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara, et al., (1989) *Proc. Natl. Acad. Sci. USA* 86:5673-5677; Loh, et al., (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOS: 1, 3, 5, 7, 9, 11, 13, 15, 17, 19, 21 and 23 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a WUS polypeptide, preferably a substantial portion of a plant WUS polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOS: 1, 3, 5, 7, 9, 11, 13, 15, 17, 19, 21, and 23 and the complement of such nucleotide sequences; and amplifying a nucleic acid fragment (preferably a cDNA inserted in a cloning vector) using the oligonucleotide primer. The amplified nucleic acid fragment preferably will encode a portion of a WUS polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering development (e.g., the initiation and maintenance of meristem apical initials) in those plants.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones, et al., (1985) *EMBO J.* 4:2411-2418; De Almeida, et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an isolated polypeptide selected from the group consisting of: (a) a polypeptide of at least 50 amino acids having at least 70% identity based on the Clustal method of alignment when compared to a polypeptide selected from the group consisting of SEQ ID NOS: 2, 4 and 12; (b) a polypeptide of at least 100 amino acids having at least 70% identity based on the Clustal method of alignment when compared to a polypeptide selected from the group consisting of SEQ ID NOS: 14, 16, 18 and 20; (c) a polypeptide of at least 180 amino acids having at least 70% identity based on the Clustal method of alignment when compared to a polypeptide of SEQ ID NO: 24; (d) a polypeptide of at least 230 amino acids having at least 70% identity based on the Clustal method of alignment when compared to a polypeptide of SEQ ID NO: 22; and (e) a polypeptide of at least 100 amino acids having at least 80% identity based on the Clustal method of alignment when compared to a polypeptide selected from the group consisting of SEQ ID NOS: 6, 8 and 10.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded WUS protein. An example of a vector for high level expression of the instant polypeptides in a bacterial host is provided (Example 12).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as Map-Maker (Lander, et al., (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, et al., (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see, Hoheisel, et al., In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred K B; see, Laan, et al., (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield, et al., (1993) *Genomics* 16:325-332), allele-specific ligation (Landegren, et al., (1988) *Science* 241:1077-1080), nucleotide extension reactions (Sokolov (1990) *Nucleic Acids Res.* 18:3671), Radiation Hybrid Mapping (Walter, et al., (1994) *Nat. Genet.* 7:22-28) and Happy Mapping (Dear and Cook (1989) *Nucleic Acids Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes, et al., (1995) *Proc. Natl. Acad. Sci. USA* 92:8149-8153; Bensen, et al., (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see, Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*) and soybean (*Glycine max*) tissues were prepared. The characteristics of the libraries are described below.

TABLE 2 cDNA Libraries from Corn and Soybean

| Library | Tissue | Clone |
|---|---|---|
| cpg1c | Corn Pooled BMS Treated with Chemicals Related to RNA, DNA Synthesis* | cpg1c.pk006.b16 |
| cpi1c | Corn Pooled BMS Treated with Chemicals Related to Biochemical Compound Synthesis** | cpi1c.pk012.p19 |

TABLE 2-continued cDNA Libraries from Corn and Soybean

| Library | Tissue | Clone |
|---|---|---|
| p0016 | Corn Tassel Shoots, Pooled, 0.1-1.4 cm | p0016.ctsas50r |
| p0058 | Sweet Corn Hybrid (Honey N Pearl) Shoot Culture | p0058.chpab57r |
| p0083 | Corn Whole Kernels 7 Days After Pollination | p0083.cldev71r |
| scr1c | Soybean Embryogenic Suspension Culture Subjected to 4 Vacuum Cycles and Collected 12 Hrs Later | scr1c.pk001.d2 |
| ses4d | Soybean Embryogenic Suspension 4 Days After Subculture | ses4d.pk0033.c8 |
| sgs5c | Soybean Seeds 4 Days After Germination | sgs5c.pk0002.f2 |
| ssm | Soybean Shoot Meristem | ssm.pk0060.h4 |

*Chemicals used included hydroxyurea, aphidicolin, HC-toxin, actinomysin D, all of which are commercially available from Calbiochem-Novabiochem Corp. (1-800-628-8470)
**Chemicals used included sorbitol, egosterol, taxifolin, methotrexate, D-mannose, D-galactose, alpha-amino adipic acid, ancymidol, all of which are commercially available from Calbiochem-Novabiochem Corp. (1-800-628-8470)

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see, Adams, et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding WUS protein were identified by conducting BLAST (Basic Local Alignment Search Tool; Altschul, et al., (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul, et al., (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding WUS Protein Homologs

The BLASTX search using the EST sequences from clones listed in Table 3 revealed similarity of the polypeptides encoded by the cDNAs to WUS proteins from *Arabidopsis thaliana* (NCBI GenBank Identifier (GI) Number 3785979) and *Arabidopsis thaliana* (NCBI GI Number 4090200). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Arabidopsis thaliana* WUS Proteins

| Clone | Status | BLAST pLog Score |
|---|---|---|
| Contig composed of: cpg1c.pk006.b16 cpi1c.pk012.p19 | Contig | 14.30 (NCBI GI No. 3785979) |
| p0016.ctsas50r | EST | 31.00 (NCBI GI No. 4090200) |
| p0083.cldev71r | EST | 17.40 (NCBI GI No. 3785979) |
| Contig composed of: scr1c.pk001.d2 ses4d.pk0033.c8 | Contig | 24.52 (NCBI GI No. 3785979) |

The data in Table 4 represents a calculation of the percent identity of the amino acid sequences set forth in SEQ ID NOS: 2, 6, 12 and 16 and the *Arabidopsis thaliana* (NCBI GI Number 3785979) and (NCBI GI Number 4090200) sequences. The percent identity between the amino acid sequences set forth in SEQ ID NOS: 2, 6, 12 and 16 ranged from 35-40%.

TABLE 4

Percent Identity of Amino Acid Sequences Deduced From the Nucleotide Sequences of cDNA Clones Encoding Polypeptides Homologous to *Arabidopsis thaliana* WUS Proteins

| SEQ ID NO. | Percent Identity to |
|---|---|
| 2 | 43% (NCBI GI No. 3785979) |
| 6 | 45% (NCBI GI No. 4090200) |
| 12 | 37% (NCBI GI No. 3785979) |
| 16 | 37% (NCBI GI No. 3785979) |

The sequence of the entire cDNA insert in most of the clones listed in Table 3 was determined. Further sequencing and searching of the DuPont proprietary database allowed the identification of other corn and soybean clones encoding WUS protein. The BLASTX search using the EST sequences from clones listed in Table 5 revealed similarity of the polypeptides encoded by the cDNAs to WUS proteins from *Arabidopsis thaliana* (NCBI GI Numbers 3785979, 4090200, 4580396, 9294502 and 6091768) and *Oryza sativa* (NCBI GI Number 8099120). Shown in Table 5 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs or PCR fragment sequence ("Contig*"), or sequences encoding the entire protein derived from an EST, an FIS, a contig, or an FIS and PCR fragment sequence ("CGS"):

TABLE 5

BLAST Results for Sequences Encoding Polypeptides Homologous to WUS Proteins

| Clone | Status | NCBI GI No. | BLAST pLog Score |
|---|---|---|---|
| cpi1c.pk012.p19 (FIS) | CGS | 3785979 | 21.30 |
| p0016.ctsas50r | FIS | 4090200 | 27.00 |
| p0058.chpab57r (FIS) | CGS | 6091768 | 36.52 |
| p0083.cldev71r | FIS | 4580396 | 15.70 |
| scr1c.pk001.d2 | FIS | 3785979 | 20.04 |
| ses4d.pk0033.c8 (FIS) | CGS | 3785979 | 21.10 |
| sgs5c.pk0002.f2 (EST) | CGS | 8099120 | 23.70 |
| Contig of ssm.pk0060.h4 (FIS) NCBI GI No. 4395781 | CGS | 9294502 | 23.00 |

FIGS. 1A and 1B present an alignment of the amino acid sequences set forth in SEQ ID NOS: 4, 10, 20, 22 and 24 and the *Arabidopsis thaliana* sequence (NCBI GI Number 4090200; SEQ ID NO: 25). The data in Table 6 represents a calculation of the percent identity of the amino acid sequences set forth in SEQ ID NOS: 4, 10, 20, 22 and 24 and the *Arabidopsis thaliana* sequence (NCBI GI Number 4090200; SEQ ID NO: 25).

TABLE 6

Percent Identity of Amino Acid Sequences Deduced From the Nucleotide Sequences of cDNA Clones Encoding Polypeptides Homologous to WUS Protein

| SEQ ID NO. | Percent Identity to NCBI GI No. 4090200; SEQ ID NO: 25 |
|---|---|
| 4 | 22.7 |
| 10 | 18.2 |
| 20 | 25.0 |
| 22 | 21.6 |
| 24 | 22.2 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a WUS protein. These sequences represent the first corn and soybean sequences encoding WUS proteins known to Applicant.

Example 4

Sunflower Meristem Transformation

There are a number of published examples of meristem transformation systems for dicot species including soybean (McCabe, et al., (1988) *Plant Physiol.* 118:675-682), sunflower (Bidney, et al., (1992) *Plant Mol. Biol.* 18:301-313), and cotton (Gould, et al., 1998), where chimeric genes are delivered to cells of the meristem and then participate in formation of shoots, reproductive structures and ultimately seed. Transgene delivery is accomplished by both standard particle bombardment protocols as described for soybean or by T-DNA and *Agrobacterium* protocols as described for sunflower and cotton. The WUS gene could be delivered to dicot meristem targets for either stable or transient transformation to impact the transformation response. WUS could be delivered together with agronomic genes or be used as a conditioning treatment prior to or following the protocol for DNA delivery. The methods for sunflower meristem transformation follow.

Sunflower meristem transformation is achieved by a protocol for direct DNA delivery by particle bombardment or a protocol involving a combination of DNA-free particle bombardment followed by use of *Agrobacterium* inoculation for DNA delivery as described in Bidney, et al., (1992) *Plant Mol. Biol.* 18:301-313. Sunflower line SMF3, described in Burrus, et al., (1991) *Plant Cell Rep.* 10:161-166, is used. The explant source is dry sunflower seed that is imbibed and dissected into meristem explants. Seeds are dehulled and surface sterilized then placed in sterile petri plates on two layers of filter paper moistened with sterile distilled water for overnight imbibition in the dark at 26° C. in a Percival incubator. The next day, cotyledons and root radicle are removed and meristem explants transferred to 374E medium (MS salts, Shepard vitamins, 40 mg/l adenine sulfate, 3% sucrose, 0.5 mg/l 6-BAP, 0.25 mg/l IAA, 0.1 mg/l GA, pH 5.6, and 0.8% Phytagar). Explants are cultured for 24 hr on 374E medium in the dark at 26° C. Following this culture period, elongated primary leaves were removed to expose the apical meristem. The meristem explants were placed in the center of petri plates with 374M medium (374E with 1.2% Phytagar) in preparation for particle bombardment then back in the dark for another 24 hr period at 26° C.

Particle preparation for the *Agrobacterium* based protocol is done by suspending 18.8 mg of 1.8 μm tungsten particles or 21.6 mg of 2.0 μm gold particles in 200 μl absolute ethanol. Following particle resuspension by sonication and vigorous mixing, 10 μl of particle suspension is dropped on the center of the surface of macro-carrier. Plates of 374M medium containing sunflower meristem explants are shot twice by a DuPont Biolistics PDS1000 helium gun with vacuum drawn to 26 Hg, with 650 psi rupture discs, and at the top level in the gun. Following particle bombardment, explants are spread out on the 374M plates, inoculated with an *Agrobacterium* suspension and co-cultured in the light at 26° C. for 4 d. The *Agrobacterium* inoculating suspension is prepared by first starting a 5 ml liquid culture in 60 A medium with kanamycin (YEP medium—10 g/l Bactopeptone, 10 g/l yeast extract, 5 g/l sodium chloride, pH 7.0, and 50 mg/l kanamycin) grown to log phase ($OD_{600}$ 0.5-1.0). The log phase growth *Agrobacterium* suspension is centrifuged at 6K for 5 min and the supernatant discarded. The bacterial pellet is resuspended in inoculation medium (IM) (IM—12.5 mM MES, 1 g/l ammonium chloride, 0.3 g/l magnesium sulfate, pH 5.7) to a final calculated OD600 vis of 4.0. The inoculating *Agrobacterium* suspension is applied twice using a micro-pipette and 0.5 μl of suspension per explant. After the 4 d co-cultivation of sunflower meristem explants, the expanded bases of explants are trimmed off and they are transferred to 374C medium (374E which lacks hormones, but adds 250 mg/l cefotaxime) and cultured for two weeks in the light under 18 hr day length at 26° C.

Alternatively, a direct DNA delivery protocol can be applied to sunflower meristem explants prepared as described above. Particles are prepared as follows: to 50 µL of a 15 mg/mL 0.6 µm gold particle suspension is added (in order): 10 µL DNA (0.1 µg/uL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 500 µL 100% ethanol and resuspended in 30 µL of 100% ethanol. The DNA/particle suspension can be sonicated three times for one second each. Five µL of the DNA-coated gold particles are then loaded on each macro carrier disk. Meristem explants are bombarded as described in the previous paragraph, spread out on 374M medium, and cultured for 4 d in a Percival incubator under 18 hr of daylength at 26° C. The expanded bases of the explant are then cut off and the explant transferred to 374C medium for 2 wk of culture under the long day conditions at 26° C.

After two weeks sunflower shoots emerge from the meristem explants on 374C medium. The shoots can be scored destructively or non-destructively for the frequency of transgenic sectors per experiment and the quality of sectors with longer, wider, and deeper transgenic sectors being more desirable. They can be scored and compared to control using scorable markers such as the GUS enzyme or green fluorescence protein (GFP). Transgenic plants and seed can be obtained by adding steps to the procedure as outlined below. An assay is required such as an enzyme assay or ELISA for an agronomic protein of interest. An example is provided using the enzyme oxalate oxidase as a scorable marker. Chemical selection is not required for this transformation process.

Primary shoots following two weeks of culture on 374C medium are screened using the oxalate oxidase enzyme assay. Oxalate oxidase enzyme assays were set up using fresh leaf or cotyledon tissue to identify transformants. The assay method was done according to the protocol of Suigura, et al., (1979) *Chem. Pharm. Bull.* 27(9):2003-2007. The assay is a two step reaction in which hydrogen peroxide is generated by oxalate oxidase in the first step then detected quantitatively by a peroxidase linked color reaction in the second. The color reaction is then measured by spectrophotometer using visible light at 550 nm. The first step of the assay was initiated by grinding shoot derived leaf tissue, pooled leaf tips of 1 sample per shoot, in 0.1 M succinate buffer, pH 3.5. The extracts were centrifuged and supernatants were discarded because most of the enzyme activity is in the cell wall due to the signal peptide of oxalate oxidase. The pellet was resuspended in 0.1 M succinate buffer, pH 3.5, and 0.05 ml of an oxalic acid solution consisting of 1 mM oxalic acid dissolved in 0.1 M succinate buffer, pH 3.5. The oxalate oxidase enzyme reaction proceeded with mild agitation at room temperature (25° C.) for 4 hr. At the end of this time period the reactions were centrifuged and an aliquot of the supernatant removed and added to a volume of 1 M Tris, pH unadjusted, to adjust the samples to a final pH of 7.0 (Tris to 0.147 M) for the second reaction step of the assay. Color development was done by adding the following components in 0.2 M Tris HCl, pH 7.0, in a mixture such that listed final concentrations were achieved: horseradish peroxidase (20 µ/ml), 4-aminoantipyrine (0.165 mM), and N,N-dimethylaniline (0.33 mM). Absorbance at 500 nm was read for samples of the color development reaction. Shoots positive for oxalate oxidase activity were moved into nodal culture for plant recovery and the negative shoots were discarded.

Positive shoots were divided into nodal explants where each explant contained at least one node from which a shoot might be recovered. Nodal explants were culture for 3 d on 374G medium (374E plus 250 mg/l cefotaxime) in the light to release nodal meristems then transferred to 374C medium and cultured in the light at 26° C. for 4 weeks to allow nodal shoot development. Shoots derived from nodal culture were assayed for oxalate oxidase activity as described above. The oxalate oxidase positive shoots were moved to procedures for plant recovery in the greenhouse and the negatives were discarded.

Assay positive shoots were recovered by grafting to Pioneer sunflower hybrid 6150 grown aseptically and in-vitro on 48 P medium (½×MS salts, 0.5% sucrose, pH 5.0, 0.3% gelrite). Root-stock was prepared by surface sterilizing seed of 6150 as described above for SMF3 then imbibing in the light at 26° C. for 4 days. Following this initial germination step, seedlings are place in the dark on 48P medium for 4 d to elongate hypocotyls. The seedlings were then placed back into the light and could be used in the next 7-10 days for grafting. Grafting was done by first cutting the 6150 seedling in the hypocotyl region below the meristem then slicing the hypocotyl longitudinally in half at the cut site. Transgenic shoots are cut at their base to separate from the originating explant and secured on the root-stock by using a parafilm wrap. After about one week in-vitro, the grafted plants were transferred to soil and maintained under humid conditions until they could survive in drier air in the greenhouse.

Transformed T0 plants are further characterized by oxalate oxidase activity assays to verify the continued presence of an active transgene and to determine if the transgene would be present in floral tissue. If there is a sector of transformation which did not develop into a new portion of the growing T0 plant, that plant portion is trimmed off to induce floral bud initiation from axillary meristems. T0 flowers are selfed, T1 seed is recovered, and the T1 seed is germinated for T1 transgenic plant identification. Cotyledon or leaf tissue of T1 seedlings is sampled and used to assay for the scorable transgene.

Example 5

Ectopic Expression of Soybean WUS to Induce Organogenesis

In addition to testing WUS in meristem transformation, other tissue explants can be tested for the formation of adventive meristems following stable or transient transformation by WUS. The explant types are well known in the art of dicot transformation and might include hypocotyl explants, leaf explants, cotyledon explants, or immature tissues such as embryo or primary leaf as described here for sunflower. As described for meristem explants, the DNA delivery can be done by either the direct delivery of particle bombardment or by *Agrobacterium* delivery by T-DNA. Using sunflower genotype SMF3 as an example, primary leaves are isolated from meristem explants prepared as described above. After the overnight culture of dissected seeds on 374E medium, the primary leaves have elongated. These are removed and placed in the center of sterile petri plates on filters moistened with 530 medium (MS salts, B5 vitamins, 3% sucrose, 4 mg/l p-chlorophenoxyacetic acid, pH 5.8) in preparation for particle bombardment. Primary leaf explants are spread out over the center of these plates such that none are overlapping others. Particle bombardment is done exactly as described above for direct DNA delivery to meristem explants except that a sterile 70 µm nitex mesh is placed over the top of the explants to help prevent them from shifting during bombardment. The DNA delivered could include a chimeric gene, consisting of a constitutive promoter such as SCP1 combined with the selectable marker NPTII and the PINII 3' region, that allows for the preferential growth of transformed tissue. Alternatively, the WUS gene may provide a growth advantage to the tissue such that a selectable marker is not required. Following particle bombardment, the explants are cultured for 3 d on filters continuously moistened with 530 medium by adding 0.5 mL of additional liquid medium per 24 hr. They are cultured in the Percival growth chamber in the light under 18 hr daylength and at 26° C. Primary leaf explants that have shown growth are then transferred to 374E medium containing 50 mg/l kanamycin if the selectable marker gene was used and cultured for 2 to 3 wk to allow transgenic callus and shoot formation. Cultures that do not respond are transferred every two weeks to 374E with 50 mg/l kanamycin until recoverable shoots are formed. Shoots are sampled, selected, and recovered to the greenhouse as described for meristem explants above.

Sunflower primary leaves can be transformed using *Agrobacterium* by slight modifications to the protocols above. The explants on 530 medium are bombarded as described for meristem explants in the *Agrobacterium* procedure above. An *Agrobacterium* suspension is produced exactly as described for meristem explants except that the liquid culture is 25 ml instead of 5 ml. The *Agrobacterium* cells are centrifuged, the growth medium supernatant discarded, and the cells resuspended to a calculated OD600 of 0.6 in inoculation medium. Primary leaf explants are inoculated in this suspension for 10 min, then placed back on 530 medium and co-cultivated for 3 d under the growth chamber conditions described above. The explants are then transferred to 374D medium (374E, 50 mg/l kanamycin, 250 mg/l cefotaxime) and cultured for 2-3 weeks. Explants can be transferred every two weeks to fresh 374D medium until shoots can be recovered.

Example 6

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu, et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see, European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, et al., (1985) *Nature* 313:810-812) and the 3' region of the nopaline synthase gene from the T-DNA of the Ti plasmid of *Agrobacterium tumefaciens*.

The particle bombardment method (Klein, et al., (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Example 7

Transformation and Regeneration of Maize Embryos

Immature maize embryos from greenhouse donor plants are bombarded with a plasmid containing the gene of the invention operably linked to a promoter; this could be a weak promoter such as nos, an inducible promoter such as In2, or a strong promoter such as Ubiquitin plus a plasmid containing the selectable marker gene PAT (Wohlleben, et al., (1988) *Gene* 70:25-37) that confers resistance to the herbicide Bialaphos. Transformation is performed as follows.

Maize ears are harvested 8-14 days after pollination and surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560L medium 4 days prior to bombardment in the dark. Medium 560L is an N6-based medium containing Eriksson's vitamins, thiamine, sucrose, 2,4-D, and silver nitrate. The day of bombardment, the embryos are transferred to 560 Y medium for 4 hours and are arranged within the 2.5 cm target zone. Medium 560Y is a high osmoticum medium (560L with high sucrose concentration).

A plasmid vector comprising the gene of the invention operably linked to the selected promoter is constructed. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water, 10 μl (1 μg) DNA in TrisEDTA buffer (1 μg total), 100 μl 2.5 M $CaCl_2$, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 μl 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are positioned 2 levels below the stopping plate for bombardment in a DuPont Helium Particle Gun. All samples receive a single shot at 650 PSI, with a total of ten aliquots taken from each tube of prepared particles/DNA. As a control, embryos are bombarded with DNA containing the PAT selectable marker as described above without the gene of invention.

Following bombardment, the embryos are kept on 560Y medium, an N6 based medium, for 2 days, then transferred to 560R selection medium, an N6 based medium containing 3 mg/liter Bialaphos, and subcultured every 2 weeks. After approximately 10 weeks of selection, selection-resistant callus clones are sampled for PCR and activity of the gene of interest. In treatments containing the WUS gene, growth is stimulated and transformation frequencies increase, relative to the control. Positive lines are transferred to 288J medium, an MS based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored for expression of the gene of interest.

Example 8

Ectopic Expression of Maize WUS to Induce Organogenesis

Using the genotype High type II as an example, embryos are isolated and cultured on 560P medium for 3-5 days. Twelve hours before bombardment these embryos are transferred to high osmotic 560Y medium. Expression cassettes containing the WUS cDNA are then co-introduced into the scutella of these embryos along with an expression cassette containing the Bar or Pat gene using methods well described in the art for particle gun transformations. Twelve to 24 hours following bombardment embryos are then transferred back to 560P culture medium and incubated in the dark at 26° C. After one week of culture these embryos are moved to 560R selection medium. Cultures are then transferred every two weeks until transformed colonies appear. Expression of WUS will stimulate adventive meristem (shoot) formation. This will be apparent when the cultures are compared to controls (transformed without the WUS cDNA or non-induced). Using either inducible expression cassettes, tissue specific promoters, or promoters of varying strengths it will be possible to control the levels of expression to maximize the formation of adventive meristems. Using either non-responsive genotypes or sub-optimal culture conditions with responsive genotypes, only the transformed cells expressing the WUS cDNA will form meristems and regenerate plants. For experiments in which WUS-induced shoot proliferation occurs via ectopic meristem formation, WUS can be used as a positive selective phenotype and no selection agent is required in the media. In this manner the WUS gene can be used as a positive selective marker (only the cells expressing the cDNA will form shoot meristems) and transformants can be recovered without a negative selective agent (i.e. bialaphos, basta, kanamycin, etc.).

Example 9

Transient Expression of the WUS Gene Product to Induce Shoot Organogenesis

It may be desirable to "kick start" meristem formation by transiently expressing the WUS genes product. This can be done by delivering WUS 5' capped polyadenylated RNA, expression cassettes containing WUS DNA, or WUS protein. All of these molecules can be delivered using a biolistics particle gun. For example 5' capped polyadenylated WUS RNA can easily be made in vitro using Ambion's mMessage mMachine kit. Following the procedure outlined above, RNA is co-delivered along with DNA containing an agronomically useful expression cassette. The cells receiving the RNA will immediately form shoot meristems and a large portion of these will have integrated the agronomic gene. Plants regenerated from these embryos can then be screened for the presence of the agronomic gene.

Example 10

Maize Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival. Transformation of a meristem cell with a WUS sequence under the expression of a promoter active in the apical meristem (either meristem-specific or constitutive) would allow the transformed cells to re-direct the initiation of new apical initials driving the meristem towards homogeneity and minimizing the chimeric nature of the plant body. To demonstrate this, the WUS sequence is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem up on a high sucrose maturation medium (see, Lowe, et al., (1997) In *Genetic Biotechnology and Breeding of Maize and Sorghum*, A S Tsaftaris, ed., Royal Society of Chemistry, Cambridge, UK, pp 94-97). The WUS expression cassette along with a reporter construct such as Ubi:GUS:pinII can then be co-delivered (preferably 24 hours after isolation) into the exposed apical dome using conventional particle gun transformation protocols. As a control the WUS construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the WUS sequence in meristem cells, through formation of new apical initials, will result in broader sectors or completely transformed meristems increasing the probability of germ-line transformation. Integration and expression of the WUS sequence will impart a competitive advantage to expressing cells resulting in a progressive enlargement of the transgenic sector. Due to the WUS-induced maintenance of apical initials and growth of their transformed derivatives, they will supplant wild-type meristem cells as the plant continues to grow. The result will be both enlargement of transgenic sectors within a given cell layer (i.e. periclinal expansion) and into adjacent cell layers (i.e. anticlinal invasions). As cells expressing the WUS gene occupy an increasingly large proportion of the meristem, the frequency of transgene germline inheritance goes up accordingly. Using WUS in this manner to target meristems will increase transformation rates, relative to control treatments. Coleoptilar-stage embryos used as a source of meristems is used as an example, but other meristem sources could be used as well, for example immature influorescences.

Example 11

Expression of Chimeric Genes in Dicot Cells

A seed-specific expression cassette composed of the promoter and transcription terminator from the gene encoding the βsubunit of the seed storage protein phaseolin from the bean *Phaseolus vulgaris* (Doyle, et al., (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12

Expression of Chimeric Genes in Microbial Cells

The cDNAs encoding the instant polypeptides can be inserted into the T7 *E. coli* expression vector pBT430. This vector is a derivative of pET-3a (Rosenberg, et al., (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier, et al., (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 13

Use of Flp/Frt System to Excise the WUS Cassette

In cases where the WUS gene has been integrated and WUS expression is useful in the recovery of maize trangenics (i.e., under conditions where continuous expression of WUS promotes adventive meristem formation), but is ultimately not desired in the final product, the WUS expression cassette (or any portion thereof that is flanked by appropriate FRT recombination sequences) can be excised using FLP-mediated recombination (see, U.S. patent application Ser. No. 08/972,258 filed Nov. 18, 1997).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated polynucleotide comprising a nucleotide sequence encoding a WUSCHEL polypeptide containing a homeodomain, wherein the polypeptide has an amino acid sequence of at least 95% sequence identity over its entire length to SEQ ID NO: 4, based on the CLUSTAL alignment method using default parameters of KTUPLE 1, GAP PENALTY=3, WINDOW=5 and DIAGONALS SAVED=5, and wherein the polypeptide is capable of stimulating in vitro growth of plant tissue.

2. The isolated polynucleotide of claim 1, wherein the amino acid sequence of the WUSCHEL polypeptide comprises SEQ ID NO: 4.

3. The isolated polynucleotide of claim 1, wherein the nucleotide sequence comprises SEQ ID NO: 3.

4. A transgenic plant or transgenic seed therefrom comprising a recombinant DNA construct comprising the polynucleotide of claim 1 operably linked to at least one regulatory sequence.

5. The plant of claim 4, wherein the plant is selected from the group consisting of corn, soybean, wheat, rice, alfalfa, sunflower, canola, and cotton.

6. A method for inducing meristem proliferation in a plant cell comprising:
(a) introducing into a plant cell the polynucleotide of claim 1 operably linked to a regulatory sequence operable in the plant cell; and,
(b) expressing the polynucleotide for a time sufficient to induce meristem proliferation.

7. The method of claim 6 wherein the polynucleotide is integrated into the plant cell genome to produce a transformed plant cell comprising the polynucleotide.

8. The method of claim 7 further comprising growing the transformed plant cell under plant growing conditions to produce a regenerated plant.

9. A method to stimulate plant cell growth, wherein the method comprises:
(a) introducing into a plant cell the isolated polynucleotide of claim 1 operably linked to a regulatory sequence operable in the plant cell; and,
(b) expressing the polynucleotide in the plant cell;
wherein plant cells expressing the polynucleotide show stimulated plant cell growth as compared to control plant cells that do not have or express the polynucleotide.

10. The method of claim 9 further comprising growing the plant cell under plant growing conditions to produce a regenerated plant.

11. The transgenic plant or the transgenic seed of claim 4, wherein the at least one regulatory sequence is an inducible promoter sequence.

12. The method claim of any one of of claim 6 or 9, wherein the at least one regulatory sequence is an inducible promoter sequence.

13. A recombinant DNA construct comprising the polynucleotide of claim 1 operably linked to at least one regulatory sequence.

14. The recombinant DNA construct of claim 13, wherein the at least one regulatory sequence is an inducible promoter sequence.

* * * * *

SEQUENCE LISTING

<160> NUMBER OF SEQ ID NOS: 25

<210> SEQ ID NO 1
<211> LENGTH: 462
<212> TYPE: DNA
<213> ORGANISM: Zea mays

<400> SEQUENCE: 1

```
gaggaagatc ccggaagcaa ccaaatcaga agcagaagct agagctacta gttttttgcat    60
tagcaagcag cagcgcagct atagcttctt gcactcgacc atcgatcgct acaaaccaca   120
catatagctg aagcaaatat atccacttgc ttaactggcg gtgtagtgta gctgcgatcg   180
ctgcaaacta cagggtgtag tgatcgtcga tcggctacat atcatatacc atggaggcgc   240
tgagcgggcg ggtaggcgtc aagtgcgggc ggtggaaccc tacggcggag caggtgaagg   300
tcctgacgga gctcttccgc gcggggctgc ggacgcccag cacggagcag attcagcgca   360
tctccaacca actcagcgcc tttgggaagg gggagaacaa aaacgtcctc ctaacgggtc   420
caaaacaaaa aggccgcgag cggcaacaac aaaagaagcg cc                     462
```

<210> SEQ ID NO 2
<211> LENGTH: 77
<212> TYPE: PRT
<213> ORGANISM: Zea mays

<400> SEQUENCE: 2

Met Glu Ala Leu Ser Gly Arg Val Gly Val Lys Cys Gly Arg Trp Asn
 1               5                  10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Asn Gln Leu
        35                  40                  45

Ser Ala Phe Gly Lys Gly Glu Asn Lys Asn Val Leu Leu Thr Gly Pro
    50                  55                  60

Lys Gln Lys Gly Arg Glu Arg Gln Gln Gln Lys Lys Arg
65                  70                  75

<210> SEQ ID NO 3
<211> LENGTH: 1338
<212> TYPE: DNA
<213> ORGANISM: Zea mays

<400> SEQUENCE: 3

```
gcacgaggag gaagatcccg gaagcaacca aatcagaagc agaagctaga gctactagtt    60
tttgcattag caagcagcag cgcagctata gcttcttgca ctcgaccatc gatcgctaca   120
aaccacacat atagctgaag caaatatatc cacttgctta actggcggtg tagtgtagct   180
gcgatcgctg caaactacag ggtgtagtga tcgtcgatcg gctacatatc ataaaccatg   240
gaggcgctga gcgggcgggt aggcgtcaag tgcgggcggt ggaaccctac ggcggagcag   300
gtgaaggtcc tgacggagct cttccgcgcg gggctgcgga cgcccagcac ggagcagatc   360
cagcgcatct ccaaccacct cagcgccttc ggcaaggtgg agagcaagaa cgtcttctac   420
tggttccaga accacaaggc ccgcgagcgc accaccacca gaagcgccg ccgcggcgcg   480
tcgtcgtcct cccccgacag cggcagcggc aggggaagca acaacgagga agacggccgt   540
ggtgccgcct cgcagtcgca cgacgccgac gccgacgccg acctcgtgct gcaaccgcca   600
gagagcaagc gggaggccag aagctatggc caccatcacc ggctcgtgac atgctacgtc   660
```

```
agggacgtgg tggagcagca ggaggcgtcg ccgtcgtggg agcggccgac gagggaggtg      720
gagacgctag agctcttccc cctcaagtcg tacggcgacc tcgaggcggc ggagaaggtc      780
cggtcgtacg tcagaggcat cgccgccacc agcgagcagt gcagggagtt gtccttcttc      840
gacgtctccg ccggccggga tccgccgctc gagctcaggc tctgcagctt cggtccctag      900
cagtagcagc tgatcgaccg tcgacgcatg catgcacgta ctgcgtgctg ctgtgcagtg      960
gccttgtcga acgcatcatt gtgtagtcct tgggttctag ctaataccga catgaaaaga     1020
tgtgtgagat gtggaaatac gcatatatat aagctgtaga acgtacgtac gtacgcgcgt     1080
agtatcgctg ccctaccaaa cgacgtacgt tgcataaaga atctgagagg gtcagggaat     1140
gagcatgcag ctgctgctga gatttcaact gccctttttcg ctgatctttt catcatgagg     1200
ccggatgcgc tgcgtgccac tttttttttc gttcatttat gctggtctgt gccctcatgc     1260
atggcatata cggaaattaa ttaacctttg tgctccctaa aaaaaaaaaa aaaaaaaaa      1320 aaaaaaaaaa aaaaaaaa                                                   1338
```

<210> SEQ ID NO 4
<211> LENGTH: 220
<212> TYPE: PRT
<213> ORGANISM: Zea mays

<400> SEQUENCE: 4

```
Met Glu Ala Leu Ser Gly Arg Val Gly Val Lys Cys Gly Arg Trp Asn
 1               5                  10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Thr His Leu
        35                  40                  45

Ser Ala Phe Gly Lys Val Glu Ser Lys Asn Val Phe Tyr Trp Phe Gln
    50                  55                  60

Asn His Lys Ala Arg Glu Arg His His His Lys Lys Arg Arg Arg Gly
65                  70                  75                  80

Ala Ser Ser Ser Pro Asp Ser Gly Ser Arg Gly Ser Asn Asn
                85                  90                  95

Glu Glu Asp Gly Arg Gly Ala Ala Ser Gln Ser His Asp Ala Asp Ala
            100                 105                 110

Asp Ala Asp Leu Val Leu Gln Pro Pro Glu Ser Lys Arg Glu Ala Arg
        115                 120                 125

Ser Tyr Gly His His His Arg Leu Val Thr Cys Tyr Val Arg Asp Val
    130                 135                 140

Val Glu Gln Gln Glu Ala Ser Pro Ser Trp Glu Arg Pro Thr Arg Glu
145                 150                 155                 160

Val Glu Thr Leu Glu Leu Phe Pro Leu Lys Ser Tyr Gly Asp Leu Glu
                165                 170                 175

Ala Ala Glu Lys Val Arg Ser Tyr Val Arg Gly Ile Ala Ala Thr Ser
            180                 185                 190

Glu Gln Cys Arg Glu Leu Ser Phe Phe Asp Val Ser Ala Gly Arg Asp
        195                 200                 205

Pro Pro Leu Glu Leu Arg Leu Cys Ser Phe Gly Pro
    210                 215                 220
```

<210> SEQ ID NO 5
<211> LENGTH: 720
<212> TYPE: DNA
<213> ORGANISM: Zea mays

<400> SEQUENCE: 5

```
atggcggcca atgcgggcgg cggtggagcg ggaggaggca gcggcagcgg cagcgtggct      60
gcgccggcgg tgtgccgccc cagcggctcg cggtggacgc cgacgccgga gcagatcagg     120
atgctgaagg agctctacta cggctgcggc atccggtcgc ccagctcgga gcagatccag     180
cgcatcaccg ccatgctgcg gcagcacggc aagatcgagg gcaagaacgt cttctactgg     240
ttccagaacc acaaggcccg cgagcgccag aagcgccgcc tcaccagcct cgacgtcaac     300
gtgcccgccg ccggcgcggc ggacgccacc accagccaac tcggcgtcct ctcgctgtcg     360
tcgccgccgc cttcaggcgc ggcgcctccc tcgcccaccc tcggtttata cgccgccggc     420
aatggcggcg atcggctgt gctgctggac acgagttccg actggggcag cagcggcgct     480
gccatggcca ccgagacatg cttcctgcag gtcggtgctg tagtacgttc ttttcttggg     540
cattgcgcgc agtttcacgt tcgtacgtac gagttgatcg ccgcgtcgtt ccatccaccg     600
gtatatataa ctgttaggta cggcggtgcg cgcccgcagg actacatggg cgtgacggac     660
acgggcagct cgtcgcagtg gccacgcttc tcgtcgtcgg acacgataat ggcggcggcc     720
```

<210> SEQ ID NO 6
<211> LENGTH: 238
<212> TYPE: PRT
<213> ORGANISM: Zea mays

<400> SEQUENCE: 6

```
Met Ala Ala Asn Ala Gly Gly Gly Ala Gly Gly Gly Ser Gly Ser
 1               5                  10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
        50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
                100                 105                 110

Gln Leu Gly Val Leu Ser Leu Ser Ser Pro Pro Ser Gly Ala Ala
            115                 120                 125

Pro Pro Ser Pro Thr Leu Gly Leu Tyr Ala Ala Gly Asn Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205

Gly Ala Arg Pro Gln Asp Tyr Met Gly Val Thr Asp Thr Gly Ser Ser
    210                 215                 220

Ser Gln Trp Pro Arg Phe Ser Ser Asp Thr Ile Met Ala
225                 230                 235
```

<210> SEQ ID NO 7
<211> LENGTH: 767
<212> TYPE: DNA
<213> ORGANISM: Zea mays

<400> SEQUENCE: 7

```
ccacgcgtcc gagctaggtc acagaagcgc tcaggaaggc cgctgagata gaggcatggc      60
ggccaatgcg gcggcggtg gagcgggagg aggcagcggc agcggcagcg tggctgcgcc     120
ggcggtgtgc cgcccagcg gctcgcggtg gacgccgacg ccggagcaga tcaggatgct     180
gaaggagctc tactacggct gcggcatccg gtcgcccagc tcggagcaga tccagcgcat     240
caccgccatg ctgcggcagc acggcaagat cgagggcaag aacgtcttct actggttcca     300
gaaccacaag gcccgcgagc gccagaagcg ccgcctcacc agcctcgacg tcaacgtgcc     360
cgccgccggc gcggccgacg ccaccaccag ccaactcggc gtcctctcgc tgtcgtcgcc     420
gccgccttca ggcgcggcgc ctccctcgcc caccctcggc ttctacgccg ccggcaatgg     480
cggcggatcg gctgtgctgc tggacacgag ttccgactgg ggcagcagcg cgctgccat     540
ggccaccgag acatgcttcc tgcaggtcgg tgctgtagta cgttcttttc ttgggcattg     600
cgcgcagttt cacgttcgta cgtacgagtt gatcgccgcg tcgttccatc caccggtata     660
tataactgtt aggtacggcg gtgcgcgccc gcaggactac atgggcgtga cggacacggg     720
cagctcgtcg cagtggccac gcttcgcgtc gtcggacacg ataatgg                  767
```

<210> SEQ ID NO 8
<211> LENGTH: 237
<212> TYPE: PRT
<213> ORGANISM: Zea mays

<400> SEQUENCE: 8

```
Met Ala Ala Asn Ala Gly Gly Gly Ala Gly Gly Gly Ser Gly Ser
  1               5                  10                  15

Gly Ser Val Ala Ala Pro Ala Val Cys Arg Pro Ser Gly Ser Arg Trp
                 20                  25                  30

Thr Pro Thr Pro Glu Gln Ile Arg Met Leu Lys Glu Leu Tyr Tyr Gly
             35                  40                  45

Cys Gly Ile Arg Ser Pro Ser Ser Glu Gln Ile Gln Arg Ile Thr Ala
         50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Ala
145                 150                 155                 160

Ala Met Ala Thr Glu Thr Cys Phe Leu Gln Val Gly Ala Val Arg
                165                 170                 175

Ser Phe Leu Gly His Cys Ala Gln Phe His Val Arg Thr Tyr Glu Leu
            180                 185                 190

Ile Ala Ala Ser Phe His Pro Pro Val Tyr Ile Thr Val Arg Tyr Gly
        195                 200                 205
```

```
Gly Ala Arg Pro Gln Asp Tyr Met Gly Val Thr Asp Thr Gly Ser Ser
    210                 215                 220

Ser Gln Trp Pro Arg Phe Ala Ser Ser Asp Thr Ile Met
225                 230                 235

<210> SEQ ID NO 9
<211> LENGTH: 1367
<212> TYPE: DNA
<213> ORGANISM: Zea mays

<400> SEQUENCE: 9
ccacgcgtcc gcctcgatcc atcacctttg catagcatat atagcgcagc agctcgacga      60
aacaccatct catcacatca catcagagca gagcagagca gagcatcacc cgatcccgat     120
cccgctattc ccagccttca gtagcagcag cagtacgtcg cgccctgccc atcgatccat     180
ctggctatca tacctgtcga catggaaggc ggactgagcc cggagcggca cgcggcggcg     240
gagccggtgc ggtcgcggtg gacgcccaag ccggagcaga tactcatcct cgagtccatc     300
ttcaacagcg gcatggtgaa cccgcccaag gacgagacgg tccgcatccg caagctgctg     360
gagcgcttcg gcgccgtggg cgacgccaac gtcttctact ggttccagaa ccgccgctcc     420
cgctcccgcc ggcgccagcg ccagctgcag gcgcaggcgg cggcctcctc gtcctcgtcg     480
ggatcgcccc ccacgagcgg cctcgcaccg ggacacgcga cggcttcgtc gacggcgggg     540
atgttcgcgc acggcgccac ctacggctcg tccgcgtccg cgtcctggcc gccgccgccg     600
tcgtgcgagg ggatgatggg cgacctggac tacggcggcg cgacgacct gttcgccatc      660 tcgcggcaga tgggctacgc cagcggcggt ggctccggct ccgcgtcctc ggcggccgtc     720
gcccaccacg agcagcagca gcagctttac tactcgccgt gccagccagc gagcatgacg     780
gtgttcatca atggcgtggc gacggaggtg ccgcggggc cgatcgacct gcggtccatg      840
ttcgggcagg acgtgatgct ggtgcactcc accgccggcc tcctcccgt caacgagtac      900 ggcgtgctca cgcagagcct gcagatgggc gagagctact tcctggtcac gagggctac     960 taggtagcta gctatagcac attgcattgc cgacatggag accccagagc tagctgatgc    1020
agtacacgta ctcctcctta ccatgcatgg aattggatgt tattcggatc gtcggagacg    1080
catgcatgca ttgcatgctg cagtacctag tatctctgtc tctgtgtacg tgttcttcag    1140
tgaatgtctg tcagctcttg ccgtccgtcc gtccgtccgg tgtagatcag aaaaaggagg    1200
caaagaattc gataccagca gtgtgtgtgt gtgtgtttac tatatataaa gagagagaca    1260
cacacaaaca aatagagtgt tgtacctacg acgcatccac atcgaacatc tatactaagt    1320
atgtatgtaa tgatgaatca aaaaaaaaaa aaaaaaaaa aaaaaag                   1367

<210> SEQ ID NO 10
<211> LENGTH: 253
<212> TYPE: PRT
<213> ORGANISM: Zea mays

<400> SEQUENCE: 10

Met Glu Gly Gly Leu Ser Pro Glu Arg His Ala Ala Glu Pro Val
  1               5                  10                  15

Arg Ser Arg Trp Thr Pro Lys Pro Glu Gln Ile Leu Ile Leu Glu Ser
             20                  25                  30

Ile Phe Asn Ser Gly Met Val Asn Pro Pro Lys Asp Glu Thr Val Arg
         35                  40                  45

Ile Arg Lys Leu Leu Glu Arg Phe Gly Ala Val Gly Asp Ala Asn Val
     50                  55                  60
```

```
Phe Tyr Trp Phe Gln Asn Arg Arg Ser Arg Ser Arg Arg Gln Arg
 65                  70                  75                  80

Gln Leu Gln Ala Gln Ala Ala Ser Ser Ser Ser Gly Ser Pro
                 85                  90                  95

Pro Thr Ser Gly Leu Ala Pro Gly His Ala Thr Ala Ser Thr Ala
                100                 105                 110

Gly Met Phe Ala His Gly Ala Thr Tyr Gly Ser Ala Ser Ala Ser
                115                 120                 125

Trp Pro Pro Pro Ser Cys Glu Gly Met Met Gly Asp Leu Asp Tyr
                130                 135                 140

Gly Gly Gly Asp Asp Leu Phe Ala Ile Ser Arg Gln Met Gly Tyr Ala
145                 150                 155                 160

Ser Gly Gly Gly Ser Gly Ser Ala Ser Ser Ala Ala Val Ala His His
                165                 170                 175

Glu Gln Gln Gln Gln Leu Tyr Tyr Ser Pro Cys Gln Pro Ala Ser Met
                180                 185                 190

Thr Val Phe Ile Asn Gly Val Ala Thr Glu Val Pro Arg Gly Pro Ile
                195                 200                 205

Asp Leu Arg Ser Met Phe Gly Gln Asp Val Met Leu Val His Ser Thr
                210                 215                 220

Ala Gly Leu Leu Pro Val Asn Glu Tyr Gly Val Leu Thr Gln Ser Leu
225                 230                 235                 240

Gln Met Gly Glu Ser Tyr Phe Leu Val Thr Arg Gly Tyr
                245                 250

<210> SEQ ID NO 11
<211> LENGTH: 513
<212> TYPE: DNA
<213> ORGANISM: Zea mays
<220> FEATURE:
<221> NAME/KEY: unsure
<222> LOCATION: (63)
<223> OTHER INFORMATION: n = A, T, C, or G
<220> FEATURE:
<221> NAME/KEY: unsure
<222> LOCATION: (185)
<223> OTHER INFORMATION: n = A, T, C, or G
<220> FEATURE:
<221> NAME/KEY: unsure
<222> LOCATION: (190)
<223> OTHER INFORMATION: n = A, T, C, or G
<220> FEATURE:
<221> NAME/KEY: unsure
<222> LOCATION: (297)
<223> OTHER INFORMATION: n = A, T, C, or G
<220> FEATURE:
<221> NAME/KEY: unsure
<222> LOCATION: (343)
<223> OTHER INFORMATION: n = A, T, C, or G
<220> FEATURE:
<221> NAME/KEY: unsure
<222> LOCATION: (362)
<223> OTHER INFORMATION: n = A, T, C, or G
<220> FEATURE:
<221> NAME/KEY: unsure
<222> LOCATION: (368)
<223> OTHER INFORMATION: n = A, T, C, or G
<220> FEATURE:
<221> NAME/KEY: unsure
<222> LOCATION: (387)
<223> OTHER INFORMATION: n = A, T, C, or G
<220> FEATURE:
<221> NAME/KEY: unsure
<222> LOCATION: (444)
<223> OTHER INFORMATION: n = A, T, C, or G
<220> FEATURE:
<221> NAME/KEY: unsure
```

```
<222> LOCATION: (475)
<223> OTHER INFORMATION: n = A, T, C, or G
<220> FEATURE:
<221> NAME/KEY: unsure
<222> LOCATION: (480)
<223> OTHER INFORMATION: n = A, T, C, or G
<220> FEATURE:
<221> NAME/KEY: unsure
<222> LOCATION: (487)
<223> OTHER INFORMATION: n = A, T, C, or G
<220> FEATURE:
<221> NAME/KEY: unsure
<222> LOCATION: (497)
<223> OTHER INFORMATION: n = A, T, C, or G

<400> SEQUENCE: 11
gcggtacgcg tgggcgtacc aaggtagcag gtggccgtgc tggaggggct gtacgaacac      60
ggnctgcgca cccccagcgc ggagcagata cagcagatca cgggcaggct gcggagcac     120 ggcgccatcg agggcaagaa cgtcttctac tggttccaga accacaaggc ccgccagcgc    180
cagangcagn aagcaggaca gcttcgccta cttcagcagg ctcctccgcc ggcccccgcc    240
gctgcccgtg ctctccatgc cccccgcgcc accgtaccat cacgcccgcg tcccggngcc    300
gcccgcgaat accgatgccg attggcgccg ccgccgcccg ctngcattgc aaacgaacaa    360 cnggggngc gcgttttttat cttacangaa acccattcta ctttgctgcc ccgcaagggc    420
cccctgcaaa tgccgcctaa taantacccc aagcacagca caacaacaa caagnaggtn    480 aaagtcnttt tccattnccc aaaaatggaa gtt                                 513

<210> SEQ ID NO 12
<211> LENGTH: 89
<212> TYPE: PRT
<213> ORGANISM: Zea mays
<220> FEATURE:
<221> NAME/KEY: UNSURE
<222> LOCATION: (53)
<223> OTHER INFORMATION: Xaa = any amino acid
<220> FEATURE:
<221> NAME/KEY: UNSURE
<222> LOCATION: (55)
<223> OTHER INFORMATION: Xaa = any amino acid

<400> SEQUENCE: 12

Gln Val Ala Val Leu Glu Gly Leu Tyr Glu His Gly Leu Arg Thr Pro
  1               5                  10                  15

Ser Ala Glu Gln Ile Gln Gln Ile Thr Gly Arg Leu Arg Glu His Gly
             20                  25                  30

Ala Ile Glu Gly Lys Asn Val Phe Tyr Trp Phe Gln Asn His Lys Ala
         35                  40                  45

Arg Gln Arg Gln Xaa Gln Xaa Ala Gly Gln Leu Arg Leu Leu Gln Gln
     50                  55                  60

Ala Pro Pro Pro Ala Pro Ala Ala Arg Ala Leu His Ala Pro Arg
 65                  70                  75                  80

Ala Thr Val Pro Ser Arg Pro Arg Pro
                 85

<210> SEQ ID NO 13
<211> LENGTH: 1194
<212> TYPE: DNA
<213> ORGANISM: Zea mays

<400> SEQUENCE: 13
ccacgcgtcc gcggacgcgt gggcgaccaa ggagcaggtg gccgtgctgg aggggctgta      60
cgagcacggc ctgcgcaccc ccagcgcgga gcagatacag cagatcacgg gcaggctgcg    120
```

-continued

```
ggagcacggc gccatcgagg gcaagaacgt cttctactgg ttccagaacc acaaggcccg    180
ccagcgccag aggcagaagc aggacagctt cgcctacttc agcaggctcc tccgccggcc    240
cccgccgctg cccgtgctct ccatgccccc cgcgccaccg taccatcacg cccgcgtccc    300
ggcgccgccc gcgataccga tgccgatggc gccgccgccg cccgctgcat gcaacgacaa    360
cggcggcgcg cgtgtgatct acaggaaccc attctacgtg gctgcgccgc aggcgccccc    420
tgcaaatgcc gcctactact acccacagcc acagcagcag cagcagcagc aggtgacagt    480
catgtaccag tacccgagaa tgaaggtagc cggccaggac aagatgatga ccagggccgc    540
ggcgcaccag cagcagcagc acaacggcgc cgggcaacaa ccgggacgcg ccggccaccc    600
cagccgcgag acgctccagc tgttcccgcc tccagcccac cttcgtgctg cggcacgaca    660
aggggcgcgc cgccaacggc agtaataacg actccctgac gtcgacgtcg acggcgactg    720
cgacagcgac agcgacagcg acagcgtccg cttccatctc cgaggactcg gatggcctgg    780
agagcggcag ctccggcaag ggcgtcgagg aggcgccccg gctgccgttc tatgacttct    840
tcgggctcca gtcctccgga ggccgctgat catgggactg aggtagagcg agctcgagtg    900
atgaaagccg agccagacgt tcgtgtgatc tcgagtcgtc gtcgatggac ccggttgccg    960
ttgccttttg ttgggttatt gcatgcatgg tgtgcttcat caactactgg aagaagcctg   1020
tgccgatcga accaaaacag tttgcattgt tgagttccgt accgtcctgt agcaacaatg   1080
tagcggagaa atgctactag tagcttcttt ttaaaaaaaa aaaaaaaaaa aaaaaaaaa    1140 aaaaaaaaaa aaaaaaaaaa aaaaaaaaaa aaaaaaaaaa aaaaaaaaaa aaag         1194
```

<210> SEQ ID NO 14
<211> LENGTH: 221
<212> TYPE: PRT
<213> ORGANISM: Zea mays

<400> SEQUENCE: 14

```
Trp Ala Thr Lys Glu Gln Val Ala Val Leu Glu Gly Leu Tyr Glu His
  1               5                  10                  15

Gly Leu Arg Thr Pro Ser Ala Glu Gln Ile Gln Ile Thr Gly Arg
             20                  25                  30

Leu Arg Glu His Gly Ala Ile Glu Gly Lys Asn Val Phe Tyr Trp Phe
         35                  40                  45

Gln Asn His Lys Ala Arg Gln Arg Gln Arg Lys Gln Asp Ser Phe
     50                  55                  60

Ala Tyr Phe Ser Arg Leu Leu Arg Arg Pro Pro Leu Pro Val Leu
 65                  70                  75                  80

Ser Met Pro Pro Ala Pro Pro Tyr His His Ala Arg Val Pro Ala Pro
                 85                  90                  95

Pro Ala Ile Pro Met Pro Met Ala Pro Pro Pro Ala Ala Cys Asn
            100                 105                 110

Asp Asn Gly Gly Ala Arg Val Ile Tyr Arg Asn Pro Phe Tyr Val Ala
            115                 120                 125

Ala Pro Gln Ala Pro Pro Ala Asn Ala Ala Tyr Tyr Tyr Pro Gln Pro
        130                 135                 140

Gln Gln Gln Gln Gln Gln Val Thr Val Met Tyr Gln Tyr Pro Arg
145                 150                 155                 160

Met Glu Val Ala Gly Gln Asp Lys Met Met Thr Arg Ala Ala His
                165                 170                 175

Gln Gln Gln Gln His Asn Gly Ala Gly Gln Gln Pro Gly Arg Ala Gly
            180                 185                 190
```

```
His Pro Ser Arg Glu Thr Leu Gln Leu Phe Pro Pro Ala His Leu
        195                 200                 205

Arg Ala Ala Arg Gln Gly Ala Arg Arg Gln Arg Gln
        210                 215                 220

<210> SEQ ID NO 15
<211> LENGTH: 506
<212> TYPE: DNA
<213> ORGANISM: Glycine max
<220> FEATURE:
<221> NAME/KEY: unsure
<222> LOCATION: (19)
<223> OTHER INFORMATION: n = A, T, C, or G
<220> FEATURE:
<221> NAME/KEY: unsure
<222> LOCATION: (489)
<223> OTHER INFORMATION: n = A, T, C, or G
<220> FEATURE:
<221> NAME/KEY: unsure
<222> LOCATION: (490)
<223> OTHER INFORMATION: n = A, T, C, or G

<400> SEQUENCE: 15
caacaagcta gtactagang atggagagta gtcacagtac tgcagaggat gagagtggat     60
ggaaaggatc aagtggtgct cattcatcag tttcacgatg gagtcctaca aggagcaaa    120 tagacatgtt ggagaacttt tacaagcagg gaataaggac tcccagcact gagcaaatac   180
aacagattac ctctaggctt agggcttatg gttacatcga gggaaaaaat gtcttctact   240
ggtttcaaaa tcacaaagcg cgccaaagac agaagctcaa gcagaagcaa caaagcattg   300
catactgcaa ttgctttctt catgcctccc accccatttg ccaaaatgtt gtctgcgtcc   360
atattgtttg caaagagtg gattcagctt ttatcctcac caaccaaagg tgcttgcaag   420
tgtaggtatt agctcaaggg attgagactg gtcctttgg catgctaaag aatatgtgat    480
ggcatgcann agtgaacacc cggatt                                        506

<210> SEQ ID NO 16
<211> LENGTH: 134
<212> TYPE: PRT
<213> ORGANISM: Glycine max

<400> SEQUENCE: 16

Met Glu Ser Ser His Ser Thr Ala Glu Asp Glu Ser Gly Trp Lys Gly
  1               5                  10                  15

Ser Ser Gly Ala His Ser Ser Val Ser Arg Trp Ser Pro Thr Lys Glu
                 20                  25                  30

Gln Ile Asp Met Leu Glu Asn Phe Tyr Lys Gln Gly Ile Arg Thr Pro
             35                  40                  45

Ser Thr Glu Gln Ile Gln Gln Ile Thr Ser Arg Leu Arg Ala Tyr Gly
     50                  55                  60

Tyr Ile Glu Gly Lys Asn Val Phe Tyr Trp Phe Gln Asn His Lys Ala
 65                  70                  75                  80

Arg Gln Arg Gln Lys Leu Lys Gln Lys Gln Gln Ser Ile Ala Tyr Cys
                 85                  90                  95

Asn Cys Phe Leu His Ala Ser His Pro Ile Cys Gln Asn Val Val Cys
            100                 105                 110

Val His Ile Val Cys Lys Arg Val Asp Ser Ala Phe Ile Leu Thr Asn
        115                 120                 125

Gln Arg Cys Leu Gln Val
    130
```

<210> SEQ ID NO 17
<211> LENGTH: 844
<212> TYPE: DNA
<213> ORGANISM: Glycine max

<400> SEQUENCE: 17

```
gcacgagagt cacagtactg cagaggatga gagtggatgg aaaggatcaa gtggtgctca      60
ttcatcagtt tcacgatgga gtcctacaaa ggagcaaata gacatgttgg agaactttta     120
caagcaggga ataaggactc ccagcactga gcaaatacaa cagattaccct ctaggcttag    180
ggcttatggt tacatcgagg gaaaaaatgt cttctactgg tttcaaaatc acaaagcgcg     240
ccaaagacag aagctcaagc agaagcaaca agcattgca tactgcaatt gctttcttca     300
tgcctcccac cccatttgcc aaaatgttgt ctgcgctcca tattgtttgc aaaagagtgg    360
attcagcttt tatcctcacc aaccaaaggt gcttgcaagt gtaggtatta gctcaaggat    420
tgagactggg tcctttggca tgctaagaat atgtgatggc atgcagagtg aacacccgga    480
ttataactat agcaccagta accgtgaagc cttaactcta tttcctcttc atccaaccgg    540
tattttggaa gaaaaaacaa ctcatcactc tgttgatgtc accgacaaat cttttgtttc    600
tattgctgtt gacgaaaatg gtcatcttgg aaatcaaccc tgctttaatt ttcagtactg    660
aagaacgaag gtatcgagat agtgattaag tatcatcgac caaaactact aacactgtac    720
tactactttc tttgagtagc tcgttgttca tcttcgaaat gagttttatc taattggata    780
ttgagtttaa cgtagtaaaa aaaaaaaaaa aaaaaaaaa aaaaaaaaaa aaaaaaaaaa     840
aaaa                                                                 844
```

<210> SEQ ID NO 18
<211> LENGTH: 217
<212> TYPE: PRT
<213> ORGANISM: Glycine max

<400> SEQUENCE: 18

Ser His Ser Thr Ala Glu Asp Glu Ser Gly Trp Lys Gly Ser Ser Gly
 1               5                  10                  15

Ala His Ser Ser Val Ser Arg Trp Ser Pro Thr Lys Glu Gln Ile Asp
                20                  25                  30

Met Leu Glu Asn Phe Tyr Lys Gln Gly Ile Arg Thr Pro Ser Thr Glu
            35                  40                  45

Gln Ile Gln Gln Ile Thr Ser Arg Leu Arg Ala Tyr Gly Tyr Ile Glu
        50                  55                  60

Gly Lys Asn Val Phe Tyr Trp Phe Gln Asn His Lys Ala Arg Gln Arg
65                  70                  75                  80

Gln Lys Leu Lys Gln Lys Gln Ser Ile Ala Tyr Cys Asn Cys Phe
                85                  90                  95

Leu His Ala Ser His Pro Ile Cys Gln Asn Val Val Cys Ala Pro Tyr
            100                 105                 110

Cys Leu Gln Lys Ser Gly Phe Ser Phe Tyr Pro His Gln Pro Lys Val
        115                 120                 125

Leu Ala Ser Val Gly Ile Ser Ser Arg Ile Glu Thr Gly Ser Phe Gly
    130                 135                 140

Met Leu Arg Ile Cys Asp Gly Met Gln Ser Glu His Pro Asp Tyr Asn
145                 150                 155                 160

Tyr Ser Thr Ser Asn Arg Glu Ala Leu Thr Leu Phe Pro Leu His Pro
                165                 170                 175

Thr Gly Ile Leu Glu Glu Lys Thr Thr His His Ser Val Asp Val Thr

```
            180                 185                 190
Asp Lys Ser Phe Val Ser Ile Ala Val Asp Glu Asn Gly His Leu Gly
        195                 200                 205

Asn Gln Pro Cys Phe Asn Phe Gln Tyr
        210                 215

<210> SEQ ID NO 19
<211> LENGTH: 741
<212> TYPE: DNA
<213> ORGANISM: Glycine max

<400> SEQUENCE: 19
gcacgagaac aagctagtac tagaagatgg agagtcacag tagtgatgct gaggcggaga      60
atgtaaggac tcattcatca gtttcacggt ggagtcctac aaaggagcaa atagacatgt     120
tagagaacct ttacaagcag ggaataagga ctcccagcac tgagcaaata aacagatta     180 cctctaggct cagggcttat ggtcacatcg agggaaagaa tgtcttctac tggtttcaaa     240
atcacaaagc tcgtcaaaga cagaagctga tgaagcaaca aaccattgca tattccaatc     300
gctttcttcg tgcctcccac cccatttgcc aaaatgttgc ctgcgctcca tattgtttgc     360
aacggagtgg attcagcttt tatcctcaac aatcgaaggt gcttgcaagt ggaggtataa     420
gttcaactgg gcctttaggc atgcaaagaa tgtttgatgg catgcagagt agtgaacacc     480
cggattgtaa ccgtgaagtc ttaactctct ttcctcttca tccaaccggc attttgaaag     540
aaaaaacaac tcatcaagtg ccttcccttg cttcaacttc tgttgttgct gttgatgaag     600
atggtcatct tggaaatcag cccttcttta atttttttcac tactgaacca aggtcgagag     660
agtgattagg tgttaattgt cattgaccaa aaaaacaact aacatggcac actttgagt      720 aaaaaaaaaa aaaaaaaaa a                                                741

<210> SEQ ID NO 20
<211> LENGTH: 212
<212> TYPE: PRT
<213> ORGANISM: Glycine max

<400> SEQUENCE: 20

Met Glu Ser His Ser Ser Asp Ala Glu Ala Glu Asn Val Arg Thr His
  1               5                  10                  15

Ser Ser Val Ser Arg Trp Ser Pro Thr Lys Glu Gln Ile Asp Met Leu
                 20                  25                  30

Glu Asn Leu Tyr Lys Gln Gly Ile Arg Thr Pro Ser Thr Glu Gln Ile
             35                  40                  45

Gln Gln Ile Thr Ser Arg Leu Arg Ala Tyr Gly His Ile Glu Gly Lys
         50                  55                  60

Asn Val Phe Tyr Trp Phe Gln Asn His Lys Ala Arg Gln Arg Gln Lys
 65                  70                  75                  80

Leu Met Lys Gln Gln Thr Ile Ala Tyr Ser Asn Arg Phe Leu Arg Ala
                 85                  90                  95

Ser His Pro Ile Cys Gln Asn Val Ala Cys Ala Pro Tyr Cys Leu Gln
                100                 105                 110

Arg Ser Gly Phe Ser Phe Tyr Pro Gln Gln Ser Lys Val Leu Ala Ser
            115                 120                 125

Gly Gly Ile Ser Ser Thr Gly Pro Leu Gly Met Gln Arg Met Phe Asp
        130                 135                 140

Gly Met Gln Ser Ser Glu His Pro Asp Cys Asn Arg Glu Val Leu Thr
145                 150                 155                 160
```

```
Leu Phe Pro Leu His Pro Thr Gly Ile Leu Lys Glu Lys Thr Thr His
                165                 170                 175

Gln Val Pro Ser Leu Ala Ser Thr Ser Val Val Ala Val Asp Glu Asp
            180                 185                 190

Gly His Leu Gly Asn Gln Pro Phe Phe Asn Phe Phe Thr Thr Glu Pro
        195                 200                 205

Arg Ser Arg Glu
    210

<210> SEQ ID NO 21
<211> LENGTH: 906
<212> TYPE: DNA
<213> ORGANISM: Glycine max

<400> SEQUENCE: 21
accagctaaa attaagcatg aaggtgcatc agttcgcacg tggattctgg gagcacgaac      60 cctcccctcac actcgggtgc aaacgcttac gccccttgc ccccaagctt ccaacaccg     120 acaccatttc tccacctcat catcctgtta caaccttcga cctcaagagc ttcatcaaac    180
ctgaaagtgc ctccagaaaa cttggaattg atcctccga tgataatact aataagagag     240
acccatcttc accccagggc caggctgaaa cgcatattcc aggagggaca cggtggaatc    300
cgactcaaga acaaataggg atattggaga tgctgtacag aggagggatg cgaactccga    360
atgctcaaca aatagagcag atcacagcac agcttagcaa gtacggcaag atcgaaggga    420
agaacgtgtt ctattggttc caaaaccaca agcacgcga gagacagaag cagaagcgta     480
acaacytagg ccttgctcat agtcctcgta ctactctcac cacttcaccc cccttagtt    540 gttgtgtaat taccactatg gacaccacaa acgggggga agtagtagaa agagaggagg    600
aagatagccc gttgaagaag tgtaggagct gggcgtttga gtacttggaa gaccaaagag    660
aggaggaaca tagaactctg gagcttttcc cattgcaccc ggaaggcaga tgaaggggtt    720
tgttttaatt gtttgaccaa tttaacgaga aatattttta gcttttaatt aattgtttct    780 gaaccctttca ggctgattgg aatgtatgtg ctttaattag tttggtttag tttttcatca    840
ctttcttctt tggttgtgtt gggaagaag aaaacacaaa gtcgtctaca aaaaaaaaaa     900
aaaaaa                                                                906

<210> SEQ ID NO 22
<211> LENGTH: 231
<212> TYPE: PRT
<213> ORGANISM: Glycine max

<400> SEQUENCE: 22

Met Lys Val His Gln Phe Ala Arg Gly Phe Trp Glu His Glu Pro Ser
  1               5                  10                  15

Leu Thr Leu Gly Cys Lys Arg Leu Arg Pro Leu Ala Pro Lys Leu Ser
                 20                  25                  30

Asn Thr Asp Thr Ile Ser Pro Pro His His Pro Val Thr Thr Phe Asp
             35                  40                  45

Leu Lys Ser Phe Ile Lys Pro Glu Ser Ala Ser Arg Lys Leu Gly Ile
         50                  55                  60

Gly Ser Ser Asp Asp Asn Thr Asn Lys Arg Asp Pro Ser Ser Pro Gln
 65                  70                  75                  80

Gly Gln Ala Glu Thr His Ile Pro Gly Gly Thr Arg Trp Asn Pro Thr
                 85                  90                  95

Gln Glu Gln Ile Gly Ile Leu Glu Met Leu Tyr Arg Gly Gly Met Arg
            100                 105                 110
```

```
Thr Pro Asn Ala Gln Gln Ile Glu Gln Ile Thr Ala Gln Leu Ser Lys
            115                 120                 125
Tyr Gly Lys Ile Glu Gly Lys Asn Val Phe Tyr Trp Phe Gln Asn His
        130                 135                 140
Lys Ala Arg Glu Arg Gln Lys Gln Lys Arg Asn Asn Leu Gly Leu Ala
145                 150                 155                 160
His Ser Pro Arg Thr Thr Leu Thr Thr Ser Pro Pro Phe Ser Cys Cys
                165                 170                 175
Val Ile Thr Thr Met Asp Thr Thr Lys Arg Gly Glu Val Val Glu Arg
            180                 185                 190
Glu Glu Glu Asp Ser Pro Leu Lys Lys Cys Arg Ser Trp Ala Phe Glu
        195                 200                 205
Tyr Leu Glu Asp Gln Arg Glu Glu His Arg Thr Leu Glu Leu Phe
    210                 215                 220
Pro Leu His Pro Glu Gly Arg
225                 230

<210> SEQ ID NO 23
<211> LENGTH: 904
<212> TYPE: DNA
<213> ORGANISM: Glycine max

<400> SEQUENCE: 23
cagcatgaag gtgcatcagt tcacacgtgg attaatctgg gagcacgaac ctttcctcac      60
acttggctgc aagagattac gccctcttgc tcccaagctt cccaaccaca aaactatcac     120
taccccttc gatctcaaga gcttcatcag gcccgaaagt ggccccagaa acccgtttc      180
ctctgacgac actaagaagg atccaccttc accccaaggc cagattgaaa cgcacccagg     240
agggacacgg tggaatccta cgcaagaaca gataggcata ttggagatgt tgtacaaagg     300
agggatgcga actccgaatg ctcaacagat agagcagatc actgtccagc ttggaaagta     360
cggcaagatc gaagggaaga acgtgttcta ttggtttcag aatcacaaag cacgcgagag     420
acaaaagcag aagcgcagca gccttgcatc ttctcatagt cctcgaactc ccacaattca     480
cagtgttgtt acttcggaga caacaagggg ggaagtggta gagagagatc acgaggaaga     540
tagtccgtac aagaagaagt gcaggagatg ggtatttgac tgcttggaag aacaaaacat     600
gtcatcacct tgtgaacaag gaacataga aactctggag cttttcccat tgcacccgga     660
aggcagatga aggggtttga gtttgattga ccatttatct atcatttttc actttgcttt     720
agttccgaat cgcagctgat tattgaatga atgtggttta attaatttgc tttactttc      780
ttttctct gtattgggaa agaagaaga caaagttgtc tctgatctgt actcttccac     840
ttaatgctat tcctgacttt ggaaccaaaa aaaaaaaaa aaaactcgga gagagcgaac     900
tagt                                                                  904

<210> SEQ ID NO 24
<211> LENGTH: 221
<212> TYPE: PRT
<213> ORGANISM: Glycine max

<400> SEQUENCE: 24

Met Lys Val His Gln Phe Thr Arg Gly Leu Ile Trp Glu His Glu Pro
1               5                   10                  15
Phe Leu Thr Leu Gly Cys Lys Arg Leu Arg Pro Leu Ala Pro Lys Leu
            20                  25                  30
Pro Asn Thr Lys Thr Ile Thr Thr Pro Phe Asp Leu Lys Ser Phe Ile
```

```
                    35                  40                  45
Arg Pro Glu Ser Gly Pro Arg Lys Pro Val Ser Ser Asp Asp Thr Lys
 50                  55                  60

Lys Asp Pro Pro Ser Pro Gln Gly Gln Ile Glu Thr His Pro Gly Gly
 65                  70                  75                  80

Thr Arg Trp Asn Pro Thr Gln Glu Gln Ile Gly Ile Leu Glu Met Leu
                 85                  90                  95

Tyr Lys Gly Gly Met Arg Thr Pro Asn Ala Gln Gln Ile Glu Gln Ile
            100                 105                 110

Thr Val Gln Leu Gly Lys Tyr Gly Lys Ile Glu Gly Lys Asn Val Phe
        115                 120                 125

Tyr Trp Phe Gln Asn His Lys Ala Arg Glu Arg Gln Lys Gln Lys Arg
    130                 135                 140

Ser Ser Leu Ala Ser Ser His Ser Pro Arg Thr Pro Thr Ile His Ser
145                 150                 155                 160

Val Val Thr Leu Glu Thr Thr Arg Gly Glu Val Val Glu Arg Asp His
                165                 170                 175

Glu Glu Asp Ser Pro Tyr Lys Lys Cys Arg Arg Trp Val Phe Asp
            180                 185                 190

Cys Leu Glu Glu Gln Asn Met Ser Ser Pro Cys Glu Gln Glu Glu His
        195                 200                 205

Arg Thr Leu Glu Leu Phe Pro Leu His Pro Glu Gly Arg
    210                 215                 220

<210> SEQ ID NO 25
<211> LENGTH: 291
<212> TYPE: PRT
<213> ORGANISM: Arabidopsis thaliana
<220> FEATURE:
<223> OTHER INFORMATION: NCBI GI 4090200

<400> SEQUENCE: 25

Met Glu Pro Pro Gln His Gln His His His Gln Ala Asp Gln Glu
 1               5                  10                  15

Ser Gly Asn Asn Asn Lys Ser Gly Ser Gly Tyr Thr Cys Arg
            20                  25                  30

Gln Thr Ser Thr Arg Trp Thr Pro Thr Thr Glu Gln Ile Lys Ile Leu
        35                  40                  45

Lys Glu Leu Tyr Tyr Asn Asn Ala Ile Arg Ser Pro Thr Ala Asp Gln
 50                  55                  60

Ile Gln Lys Ile Thr Ala Arg Leu Arg Gln Phe Gly Lys Ile Glu Gly
 65                  70                  75                  80

Lys Asn Val Phe Tyr Trp Phe Gln Asn His Lys Ala Arg Glu Arg Gln
                 85                  90                  95

Lys Lys Arg Phe Asn Gly Thr Asn Met Thr Thr Pro Ser Ser Ser Pro
            100                 105                 110

Asn Ser Val Met Met Ala Ala Asn Asp His Tyr His Pro Leu Leu His
        115                 120                 125

His His His Gly Val Pro Met Gln Arg Pro Ala Asn Ser Val Asn Val
    130                 135                 140

Lys Leu Asn Gln Asp His His Leu Tyr His Asn Lys Pro Tyr Pro
145                 150                 155                 160

Ser Phe Asn Asn Gly Asn Leu Asn His Ala Ser Ser Gly Thr Glu Cys
                165                 170                 175

Gly Val Val Asn Ala Ser Asn Gly Tyr Met Ser Ser His Val Tyr Gly
            180                 185                 190
```

```
Ser Met Glu Gln Asp Cys Ser Met Asn Tyr Asn Asn Val Gly Gly Gly
        195                 200                 205

Trp Ala Asn Met Asp His His Tyr Ser Ser Ala Pro Tyr Asn Phe Phe
        210             215                 220

Asp Arg Ala Lys Pro Leu Phe Gly Leu Glu Gly His Gln Asp Glu Glu
225                 230                 235                 240

Glu Cys Gly Gly Asp Ala Tyr Leu Glu His Arg Arg Thr Leu Pro Leu
            245                 250                 255

Phe Pro Met His Gly Glu Asp His Ile Asn Gly Gly Ser Gly Ala Ile
            260                 265                 270

Trp Lys Tyr Gly Gln Ser Glu Val Arg Pro Cys Ala Ser Leu Glu Leu
        275                 280                 285

Arg Leu Asn
290
```